US00PP37350P2

(12) United States Plant Patent
Dirr et al.

(10) Patent No.: US PP37,350 P2
(45) Date of Patent: Mar. 31, 2026

(54) ***DISTYLIUM* PLANT NAMED 'T3-01-22'**

(50) Latin Name: *Distylium spp.*
Varietal Denomination: T3-01-22

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 19/185,853

(22) Filed: Apr. 22, 2025

(51) Int. Cl.
*A01H 5/12* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/12
See application file for complete search history.

(56) References Cited

PUBLICATIONS https://www.nurserymag.com/article/griffith-propagation-nursery-plant-breeding/; Mar. 11, 2025; 8 pages.*

* cited by examiner

*Primary Examiner* — Kent L Bell

(57) ABSTRACT

A new and distinct cultivar of *Distylium* plant named 'T3-01-22', characterized by its upright growth habit, reddish new growth, lustrous leathery olive-green foliage, that is larger than on any known *Distylium* cultivar, its excellence as a screening plant, and tolerance of wet and dry soil. The new cultivar is a *Distylium*, typically produced as an ornamental plant.

4 Drawing Sheets

Genus and species of plant claimed: *Distylium spp.*
Variety denomination: 'T3-01-22'

BACKGROUND OF THE INVENTION

The present invention relates to a new and distinct cultivar of *Distylium* plant, botanically known as *Distylium* hybrid, a member of the Hamamelidaceae family, and hereinafter referred to by the cultivar name 'T3-01-22'.

'T3-01-22' originated as an open-pollinated seedling from seed collected from an unnamed and unpatented *Distylium* hybrid, growing in Watkinsville, Georgia. 'T3-01-22' is a *Distylium* spp. (*Distylium myricoides* x *D. racemosum*) selected in 2022 by the inventors in a cultivated environment in Watkinsville, GA.

Asexual reproduction of 'T3-01-22' by stem cuttings since 2022 has shown that all the unique features of 'T3-01-22', as herein described, are stable and reproduced true-to-type through successive generations of such asexual propagation. First propagation took place at a research nursery in Watkinsville, GA.

SUMMARY OF THE INVENTION

'T3-01-22' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'T3-01-22' from all other varieties in commerce known to the inventor:

1. Upright growth habit.
2. Reddish (183A and 184B) new growth.
3. Lustrous leathery olive-green (137A and 147B) foliage.
4. Excellence as a screening plant, that tolerates wet and dry soils.
5. Deep red (178A) flower color.
6. Largest leaves of any known *Distylium* cultivar.

PARENTAL COMPARISON

Plants of the new cultivar 'T3-01-22' are comparable to the seed parent in most horticultural characteristics. However, the new variety 'T3-01-22' differs in the following:

1. Plant habit of 'T3-01-22' is tighter and fuller than the plant habit of the seed parent.
2. Leaves of 'T3-01-22' are larger than leaves of the seed parent.

COMMERCIAL COMPARISON

Plants of the new cultivar 'T3-01-22' can be compared to the commercial cultivar 'PIIDIST-I', U.S. Plant Pat. No. 24,410, in most horticultural characteristics. However, the new variety 'T3-01-22' differs in the following:

1. Plants of 'T3-01-22' produce branches at more acute angles (around 15° to 45°), forming a more upright, plant. Plants of this comparator produces branches at angles closer to 60° to 75°, forming broader plants.
2. New growth of 'T3-01-22' is red (183A and 184B), while new growth of this comparator is yellow-green (146B).

3. The mature upper leaf surface of 'T3-01-22' is 137A olive-green, whereas the mature upper leaf surface of this comparator is dark green (147A). 26
4. Flower color of T3-01-22' is deep red (178A), while the flower color of this comparator is 187B.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Distylium*. Plants were grown and photographed in Watkinsville, GA.

DETAILED BOTANICAL DESCRIPTION

Figure 1:
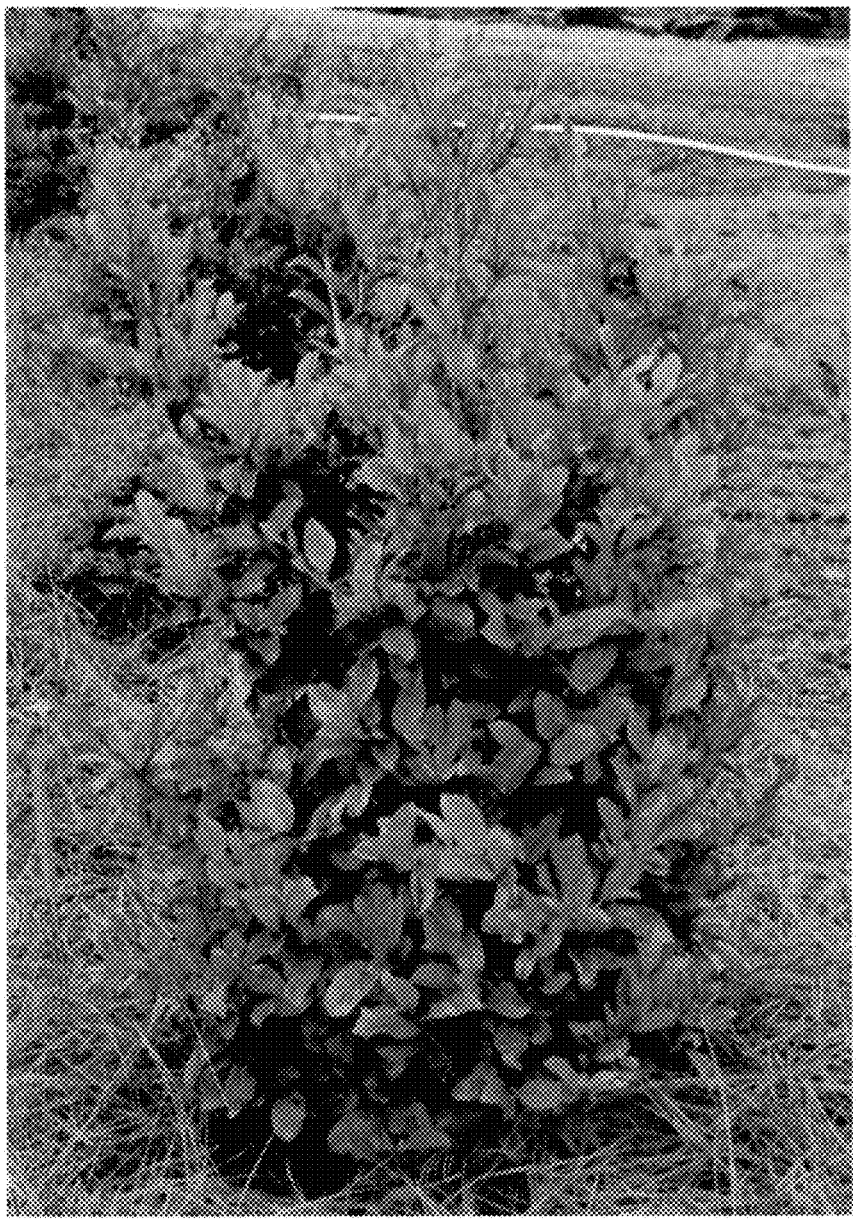
FIG. 1 illustrates the overall appearance and growth habit of a three-year-old plant of 'T3-01-22' plant in the ground.
Figure 2:
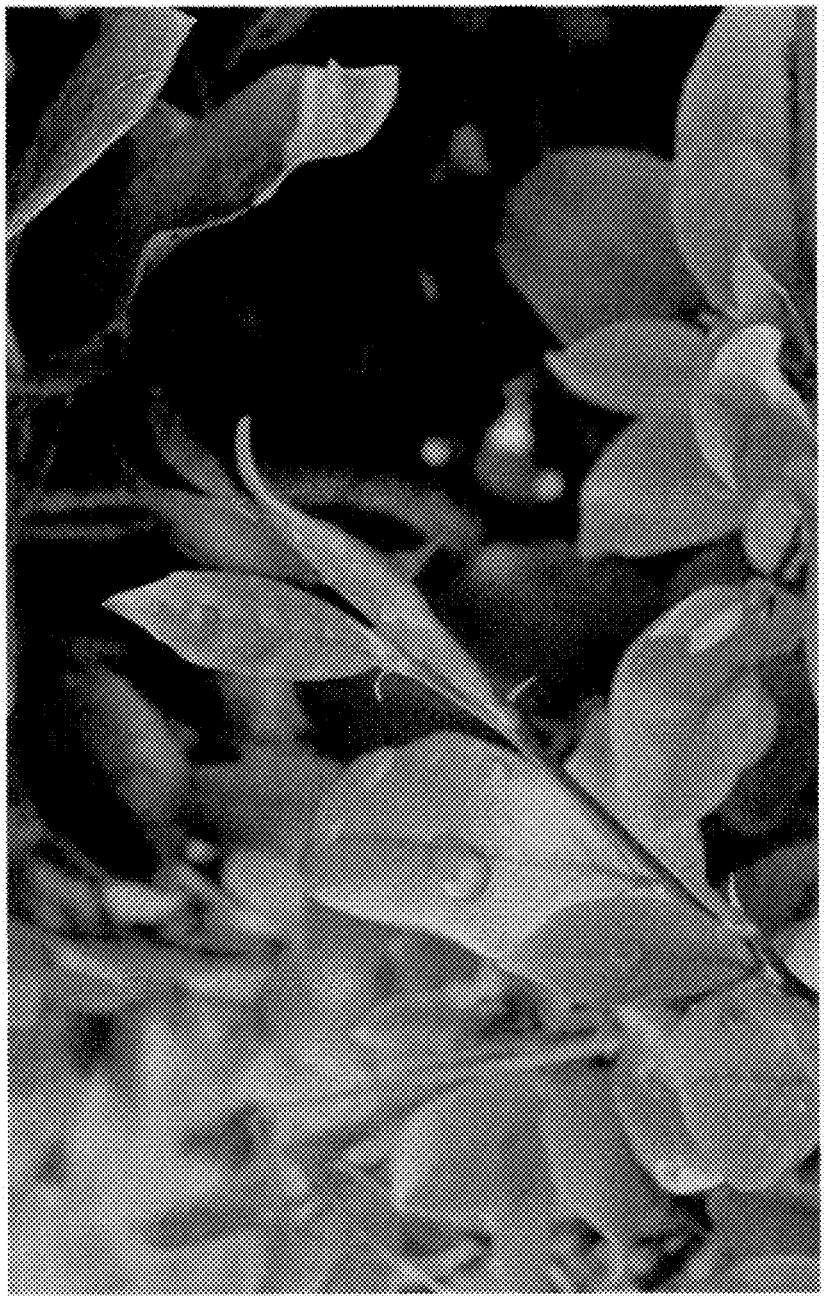
FIG. 2 illustrates a close-up of the new growth of a 'T3-01-22' plant.
Figure 3:
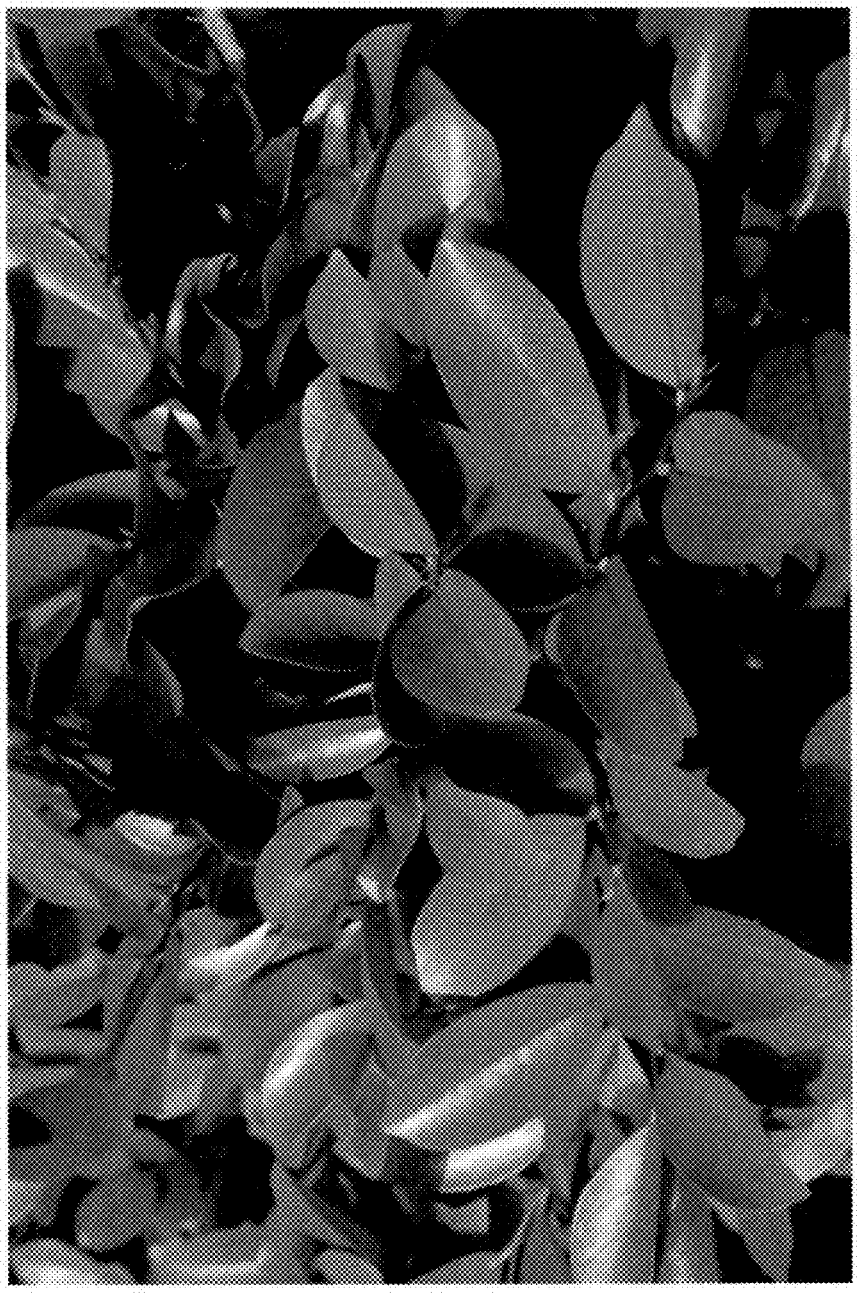
FIG. 3 illustrates the mature foliage of a three-year-old plant of 'T3-01-22'.
Figure 4:
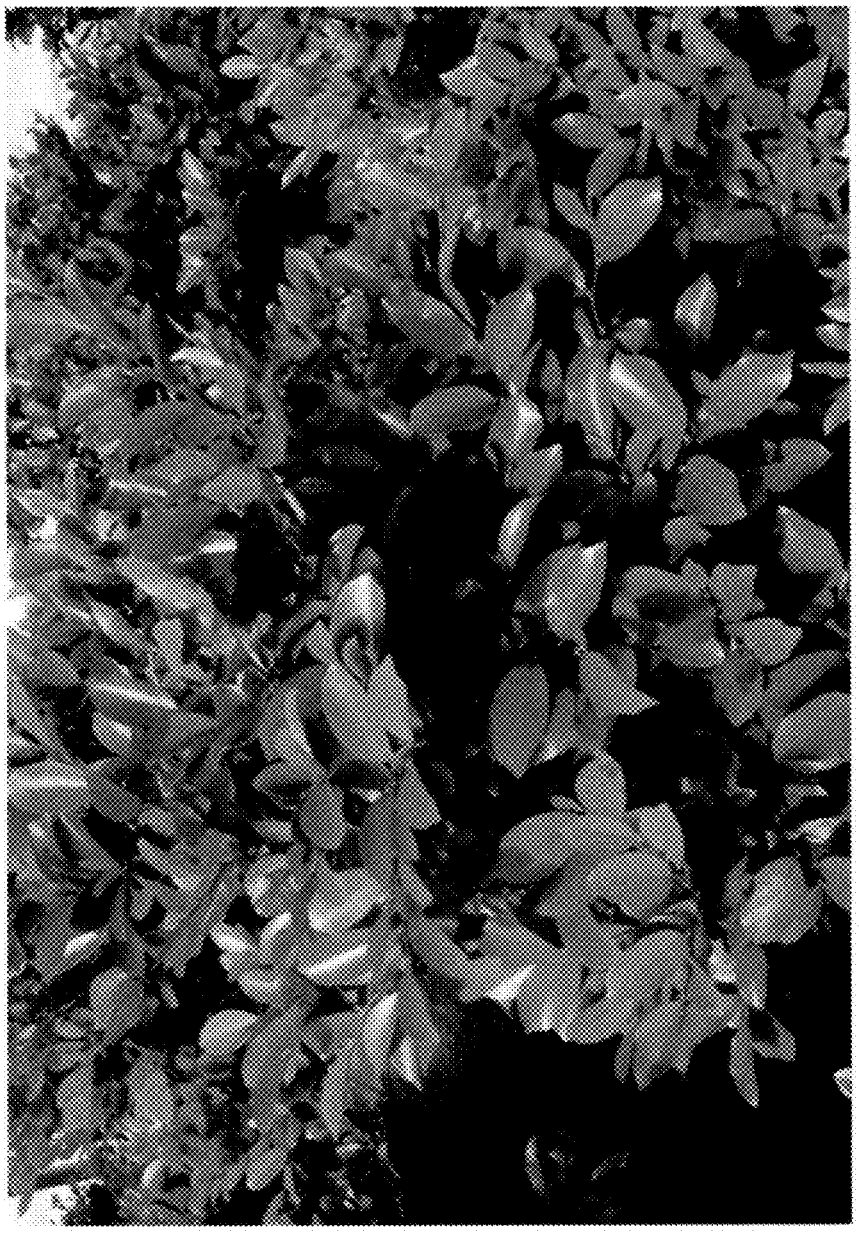
FIG. 4 illustrates a two-year-old 'T3-01-22' in a container.

In the following description, color references are made to The Royal Horticultural Society Colour Chart, 2015 Edition, except where general terms of ordinary dictionary significance are used. The plant used for the description was approximately two years old and was grown in 26.4 L containers under 50% shade under outdoor conditions in Watkinsville, GA.

Botanical classification: *Distylium* 'T3-01-22'.

PROPAGATION

Type of propagation typically used: Vegetative stem cuttings.

Time to initiate roots: About 6 weeks at 32° C. in summer.

Number of days to produce a rooted plant: About 3 months at 32° C. in summer.

Root description: Medium, well-branched, diffuse, and extensive. Colored RHS Greyed-Yellow 156A.

PLANT

Type of plant: Broadleaf evergreen shrub.

Age of plant described: 3 years old.

Container size of the plant described: 26.4 liters.

Growth habit: Broadleaf, evergreen, flowering shrub; multi-stemmed; upright growth habit. Freely branching; removal of the terminal bud enhances lateral branch development.

Height: About 94 cm.

Plant spread: About 88 cm.

First year stems:

*Length*.—About 16 cm.
*Diameter*.—About 2 mm.
*Shape*.—Round.
*Color*.—RHS Red 184B maturing to Yellow-Green 144B.
*Pubescence*.—Fine.
*Strength*.—Flexible.
*Lenticels*.—Diameter: About 1 mm. Color: RHS Brown 199B.

Second year stems:

*Length*.—56 cm.
*Diameter*.—5 mm or more.
*Shape*.—Round.
*Color*.—RHS Gray 197D.
*Pubescence*.—None.
*Strength*.—Flexible when young; less when mature.

Trunk/main stem diameter: About 2 cm at the soil line.

Trunk/main stem color: RHS Gray 197A.

Bark: Does not exfoliate, covered with many lenticels, RHS Brown 199B in color, about 1 mm in diameter.

Internode length: About 2 cm.

Vegetative buds:

*Arrangement*.—Alternate.
*Shape*.—Ovoid with fused, pubescent bud scales.
*Length*.—About 4 mm.
*Width*.—About 3 mm.
*Color*.—RHS Brown-Orange 165B.

FOLIAGE

Leaf:

*Arrangement*.—Alternate, simple.
*Average length*.—About 7 cm.
*Average width*.—About 3.5 cm.
*Shape of blade*.—Lanceolate.
*Apex*.—Acute.
*Base*.—Cuneate.
*Margin*.—Entire, occasionally undulating.
*Texture of top surface*.—Smooth, thick, leathery.
*Texture of bottom surface*.—Smooth, thick, leathery.
*Color*.—Young foliage upper side: RHS Red 183A mixed with a hint of Yellow-Green 144A. Young foliage under side: RHS Red 183A mixed with a hint of Yellow-Green 144A. Fully expanded foliage upper side: RHS Green 137A. Fully expanded foliage under side: RHS Yellow-Green 147B.
*Venation*.—Type: Pinnate. Color, upper side, midrib: RHS Red 183A. Color, under side, midrib: RHS Red 183A. Color, secondary: RHS Yellow-Green 146C.
*Petiole*.—Length: About 5 mm. Diameter: About 2 mm. Color: RHS Yellow-Green 144A, both surfaces. Pubescence: Fine, RHS Brown 199A in color.

FLOWER

Natural flowering season: Late winter, approximately January to February in Watkinsville, GA. Individual flowers are showy for approximately 1 week and are self-cleaning.

Flower type and habit: Apetalous flowers with pubescent, 5-parted calyx are borne on short racemes from the leaf axils.

Raceme length: 2.5 to 3 cm.

Raceme diameter: 1.5 cm.

Flowers per raceme: 4 to 10.

Racemes per lateral branch: 12 to 20.

Flower diameter: About 2.5 mm.

Flower height: About 5 mm.

Calyx diameter: About 2.5 mm.

Calyx depth: About 5 mm.

Calyx shape: Obovate.

Calyx color: Greyed-Red 179A all surfaces.

Persistence: Self-Cleaning.

Fragrance: None.

Pedicels:

*Length*.—About 2 mm.

*Diameter*.—About 1 to 2 mm.

*Color*.—RHS Yellow-Green 146A with pubescence colored Brown 165A.

Peduncles:

*Length*.—About 1.2 cm.

*Diameter*.—About 3 to 4 mm.

*Color*.—RHS Yellow-Green 146A with pubescence colored Brown 165A.

REPRODUCTIVE ORGANS

Stamens:

*Number*.—7 to 10.

*Filament length*.—About 3 mm.

*Filament width*.—Less than 1 mm.

*Color*.—RHS Red 185A.

*Pollen*.—Amount: Moderate. Color: RHS Yellow 158D.

Pistil:

*Position*.—Superior.

*Length*.—Approximately 1.1 mm.

*Width*.—2 mm.

*Color*.—RHS Yellow-Green 146B.

*Style*.—Number: 2 per flower. Length: 3 mm. Color: RHS Yellow-Green 146B.

*Stigma*.—Number: 2 per pistil. Length: About 6 mm. Color: RHS Red-Orange 178B. Ovary: Number: 2 per flower. Length: About 2 mm. Width: About 2 mm. Color: RHS Yellow-Green 146B.

OTHER CHARACTERISTICS

Temperature tolerance: USDA Hardiness Zone Map (2023): Zones 7-9.

Fruits and seeds: Not observed to date.

Disease/pest resistance: Disease and pest resistance: Not observed to be susceptible nor resistant to normal diseases and pests of *Distylium*.

What is claimed is:

1. A new and distinct cultivar of *Distylium* plant named 'T3-01-22', as illustrated and described herein.

* * * * *